United States Patent [19]

Gurley

[11] Patent Number: 5,366,447
[45] Date of Patent: Nov. 22, 1994

[54] PROTECTIVE SLEEVE FOR A HYPODERMIC SYRINGE

[76] Inventor: Carol A. Gurley, Rte. 2, Box 115, Marks, Miss. 38646

[21] Appl. No.: 165,174

[22] Filed: Dec. 13, 1993

[51] Int. Cl.$^5$ .............................................. A61M 5/32
[52] U.S. Cl. .................................. 604/192; 604/198; 604/263
[58] Field of Search ............... 604/110, 198, 192, 187, 604/263

[56] References Cited

U.S. PATENT DOCUMENTS

| | | | |
|---|---|---|---|
| 3,073,307 | 1/1963 | Stevens | 604/192 |
| 4,720,285 | 1/1988 | Pickhard | 604/192 |
| 4,801,295 | 1/1989 | Spencer | 604/198 |
| 4,900,311 | 2/1990 | Stern et al. | 604/198 |
| 4,932,940 | 6/1990 | Walker et al. | 604/110 |
| 4,943,282 | 7/1990 | Page et al. | 604/263 X |
| 4,966,592 | 10/1990 | Burns et al. | 604/198 |
| 4,998,924 | 3/1991 | Ranford | 604/798 |
| 5,176,656 | 1/1993 | Bayless | 604/198 |

*Primary Examiner*—John D. Yasko
*Attorney, Agent, or Firm*—Rhodes & Ascolillo

[57] ABSTRACT

A protective apparatus, for a hypodermic syringe having a barrel and a needle has an elongated sleeve slidingly engaging the barrel of the syringe. There is a L-shaped locking and guide groove on the barrel of the syringe. A locking and guide tab on an inside wall of the sleeve slidingly engages and traverses the locking and guide groove. A locking slot, in the locking and guide groove, receives and locks the locking and guide tab in place to discourage further use of the syringe by limiting further longitudinal movement of the sleeve along the barrel of the syringe. There is a first seal, in one end of the sleeve which abuts the inside wall of the sleeve and abuts an outside wall of the barrel of the syringe, to seal the one end against the barrel of the syringe. A second seal, in another end of the sleeve, seals around an outer wall of the needle when the sleeve is in a retracted position on the barrel of the syringe. The second seal also seals off the another end of the sleeve when the sleeve is in an extended position on the barrel of the syringe. A break-away needle cover is releasingly attached by a plurality of filament-like arms to the another end of the sleeve to protect the needle prior to use of the syringe.

1 Claim, 2 Drawing Sheets

PROTECTIVE SLEEVE FOR A HYPODERMIC SYRINGE

BACKGROUND OF THE INVENTION

1. Field of the Invention

This invention relates to a protective sleeve for a hypodermic syringe that locks the sleeve over the needle once the syringe has been used for its intended purpose and the syringe is ready to be disposed of. The sleeve reduces the chance of someone being accidentally stuck with the needle and becoming infected.

2. Description of the Related Art

Many inventors have attempted to solve the problem of syringe safety with varying degrees of success.

U.S. Pat. No. 4,932,940 to C. F. Walker, et al., on Jun. 12, 1990 for a Needle Guard Device describes a sleeve on a syringe that traverses a V-shaped slot. The sleeve is spring loaded in a position covering the needle. As the sleeve is pulled back exposing the needle, a pin in the slot enters the other leg of the V and when the sleeve returns to the needle covered position, a set of teeth engage a rachet and lock the sleeve in the needle covered position.

U.S. Pat. No. 4,966,592 to C. A. Burns, et al., on Oct. 30, 1990 for a Protective Sleeve for a Hypodermic Needle shows a sleeve slidingly engaged on a barrel of a syringe and having the sleeve springingly biased toward and extending beyond the distal end of the needle. There is a Y-shaped slot that locks the sleeve in a retracted, operable position.

U.S. Pat. No. 4,998,924 to A. B. Ranford on Mar. 12, 1991 for Double Sleeve Safety Syringe describes two sleeves that interact with a tab that locks the longer sleeve in an extended position enclosing the needle.

U.S. Pat. No. 5,176,656 to W. B. Bayless on Jan. 05, 1993 for an Automatically Positioned Needle Sheath for a Disposable Hypodermic Syringe shows a syringe having two sleeves. The inner sleeve has three movable shields arranged at 120 degrees. Each shield has a tab that when the sleeve is at an extended position past the distal end of the needle, it forms a barrier around the needle. The sleeve must be pulled forcibly back from the distal end of the needle in order to open the shield and expose the end of the needle.

The present invention overcomes many of the shortcomings of the related art.

SUMMARY OF THE INVENTION

Catching a transmittable disease, such as AIDS, is constantly on the minds of the health care community. Accidentally being stuck with a contaminated needle is what doctors, nurses and their assistants dread the most. Even with constant awareness and care, tragedy often strikes. The present invention is a solution to this problem. The protective apparatus of the present invention improves over the common syringe and reduces the chance of accidental puncture of the user's skin. Once a decision is reached to use the syringe, a break-away needle cover is removed by grasping the syringe in both hands and breaking the filament-like retainer arms that hold the break-away needle cover to the protective sleeve. This exposes the yet unused needle. At this time, the syringe may be used as required to fill the barrel and eject the contents therein. The barrel of the syringe has an L-shaped guide groove in its wall. The protective sleeve surrounds and slides up and down the barrel longitudinally. A locking tab attached to an inside surface of the sleeve traverses the groove. Once the needle has been contaminated by use, the sleeve is turned around the circumference of the barrel. As the tab travels out of the short leg of the L-shaped groove, it is able to be guided up the long leg of the groove which allows the sleeve to travel to an extended position placing one end of the sleeve just beyond a distal or ejection end of the now contaminated needle. Near the end of the long leg of the groove is a locking slot. The locking slot has rounded entrance or outer walls and substantially straight, vertical exit or inner walls. The locking tab is just flexible enough to slide up over the entrance walls but is not flexible enough to pass back over the straight, inner exit wall without substantial effort. Such effort should make the user aware that he or she is attempting to override a safety feature and they should reconsider their need to do so. Such an attempt will likely break off the locking tab providing evidence of an effort to disregard the purpose of the protective sleeve if the sleeve was locked after its initial use. A seal, that substantially closes off the distal end of the sleeve through which the injection end of the needle passes back through, also limits access to the needle once the sleeve is locked in place after use.

In addition to post-use safety, pre-use is a consideration. A broken tab could serve to alert someone who picks up the syringe that it may possibly be contaminated. Finding the break-away needle cover broken off by another prior to use is another indicator that might serve to alert the user that it might be wise to choose another syringe.

A first embodiment of a protective apparatus, for a hypodermic syringe having a barrel and a needle, is shown and described that has an elongated sleeve slidingly engaging the barrel of the syringe. There is a locking and guide groove on barrel of the syringe. A locking and guide tab, on an inside wall of the sleeve, slidingly engages and traverses the locking and guide groove. There is a locking slot in the locking and guide groove to receive and lock in place the locking and guide tab. There is a first seal, in one end of the sleeve that abuts the inside wall of the sleeve and abuts an outside wall of the barrel of the syringe, to seal the one end against the barrel of the syringe. A break-away needle cover is releasingly attached to another end of the sleeve to protect the needle prior to use of the syringe. The locking slot may be L-shaped. The break-away needle cover may be releasingly attached by a plurality of filament-like arms to the another end of the sleeve to protect the needle prior to use of the syringe.

It is an object of this invention to provide an improved syringe that has a readily available and easily used protective sleeve to cover the needle of the syringe once the syringe has been used for its intended purpose in order to protect someone from being stuck by the already used needle and perhaps becoming infected thereby.

DESCRIPTION OF THE PREFERRED EMBODIMENTS

Figure 1:
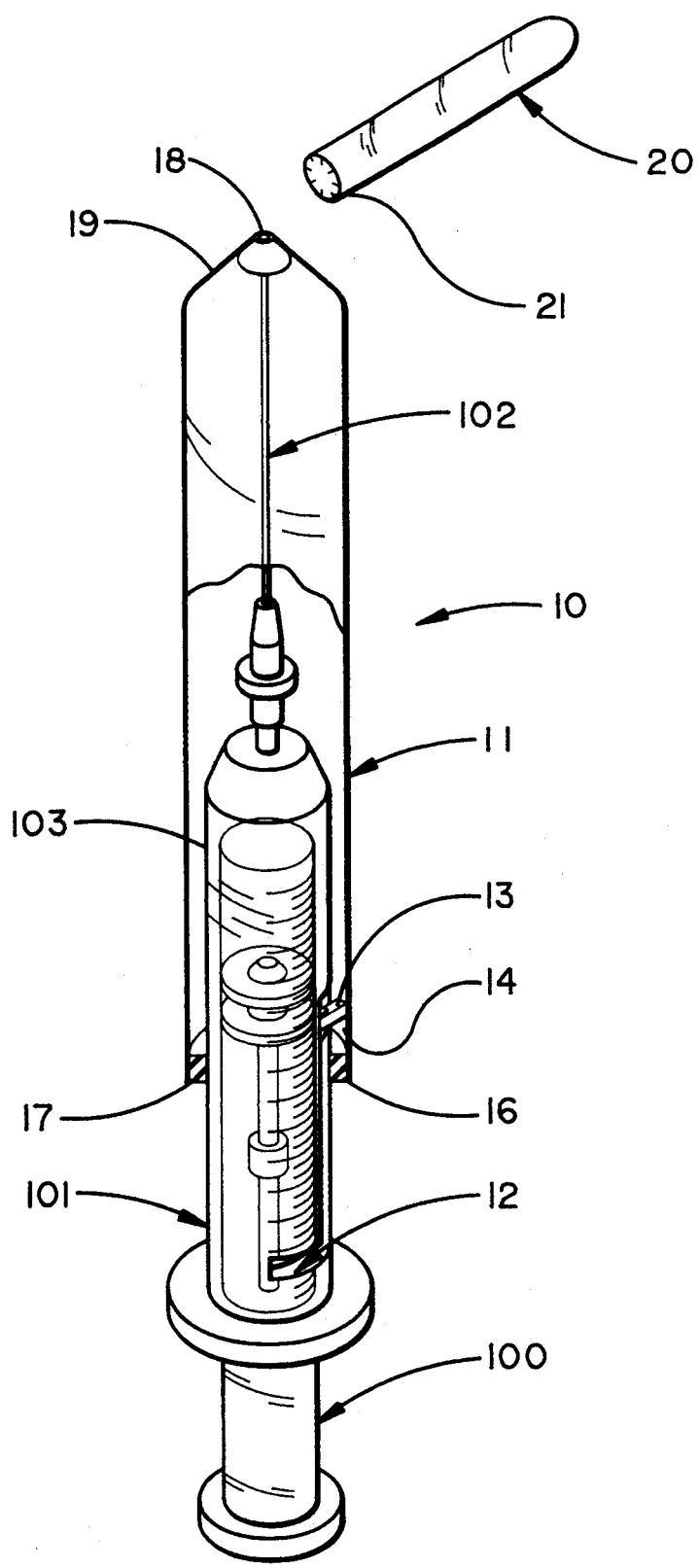
FIG. 1 is a perspective view having a partial cross-section of a Protective Sleeve for a Hypodermic Syringe shown with the break-away needle cover broken off and showing the protective sleeve in a fully extended and locked position after the syringe's use.
Figures 2, 3, 4, 6:
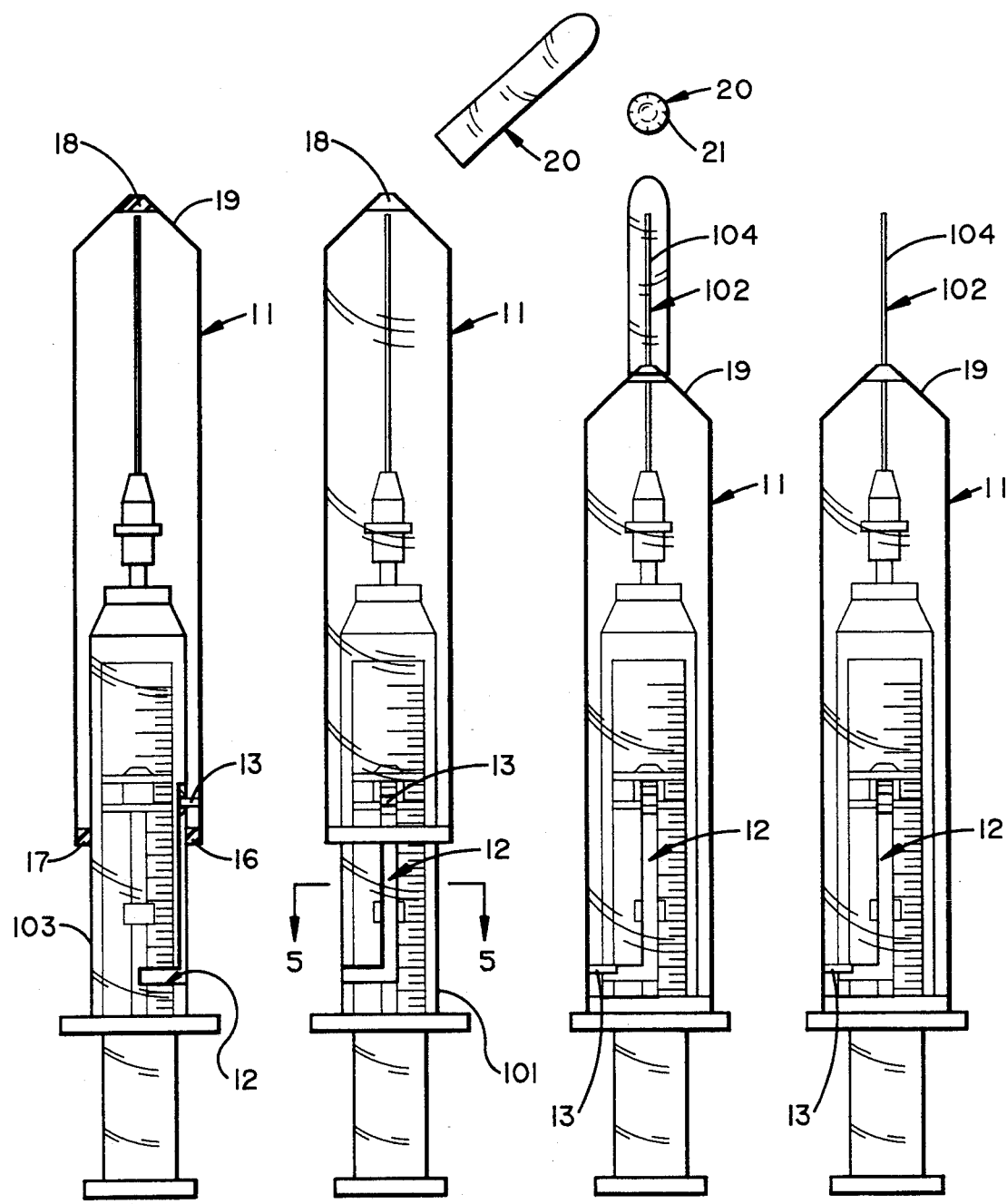
FIG. 2 is front plan view of a Protective Sleeve for a Hypodermic Syringe shown with the break-away needle cover broken off in preparation for the syringe's use.
FIG. 3 is a front plan view of a Protective Sleeve for a Hypodermic Syringe showing the break-away needle cover held in place on the one end of the sleeve by the plurality of filament-like arms.
FIG. 4 is a front plan view, with a cross-sectional view of the protective sleeve, of a Protective Sleeve for a Hypodermic Syringe showing the protective sleeve in a fully extended and locked position over the distal or fluid ejection end of the needle.
FIG. 6 is a front plan view of a Protective Sleeve for a Hypodermic Syringe showing the syringe prior to being used for an injection and showing the protective sleeve in a fully retracted position.
Figure 5:
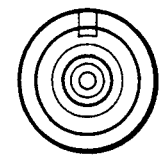
FIG. 5 is a cross-sectional view taken along line 5—5 of FIG. 2.

Referring to FIGS. 1 through 6, a protective apparatus 10, for a hypodermic syringe 100 having a barrel 101 and a needle 102, is shown that has an elongated sleeve 11 slidingly engaging the barrel 101 of the syringe 100. There is a L-shaped locking and guide groove 12 on barrel 101 of the syringe 100. A locking and guide tab 13 on an inside wall 14 of the sleeve 11 slidingly engages and traverses the locking and guide groove 12. A locking slot 15, in the locking and guide groove 12, receives and locks the locking and guide tab 13 in place to discourage further use of the syringe 100 by limiting further longitudinal movement of the sleeve 11 along the barrel 101 of the syringe 100 (See FIGS. 2 and 4). There is a first seal 16, in one end 17 of the sleeve 11 which abuts the inside wall 14 of the sleeve 11 and an outside wall 103 of the barrel 101 of the syringe 100, to seal the one end 17 against the barrel 101 of the syringe 100. A second seal 18, in another end 19 of the sleeve 11, seals around an outer wall 104 of the needle 102 when the sleeve 11 is in a retracted position (Shown in FIGS. 3 and 6) on the barrel 101 of the syringe 100. The second seal 18 also seals off the another end 19 of the sleeve 11 when the sleeve 11 is in an extended position (Shown in FIGS. 1, 2 and 4) on the barrel 101 of the syringe 100. A break-away needle cover 20 is releasingly attached (See FIG. 3) by a plurality of filament-like arms 21 to the another end 19 of the sleeve 11 to protect the needle 101 prior to use of the syringe 100.

The foregoing descriptions and drawings of the invention are explanatory and illustrative only, and various changes in shape, sizes and arrangements of parts as well certain details of the illustrated construction may be made within the scope of the appended claims without departing from the true spirit of the invention.

I claim:

1. A protective apparatus, for a hypodermic syringe having a barrel and a needle, comprising:
    (a) an elongated sleeve slidingly engaging the barrel of the syringe;
    (b) a L-shaped locking and guide groove on the barrel of the syringe;
    (c) a locking and guide tab, on an inside wall of the sleeve, slidingly engaging and traversing the locking and guide groove;
    (d) a locking slot in the locking and guide groove to receive and lock in place the locking and guide tab;
    (e) a first seal, in one end of the sleeve and abutting the inside wall of the sleeve and an outside wall of the barrel of the syringe, to seal the one end against the barrel of the syringe;
    (f) a second seal in another end of the sleeve to seal around an outer wall of the needle when the sleeve is in a retracted position on the barrel of the syringe and to seal off the another end of the sleeve when the sleeve is in an extended position on the barrel of the syringe; and
    (g) a break-away needle cover releasingly attached by a plurality of filament-like arms to the another end of the sleeve to protect the needle prior to use of the syringe.

* * * * *